United States Patent [19]

Wietfeldt

[11] Patent Number: 4,965,067

[45] Date of Patent: * Oct. 23, 1990

[54] ORAL COMPOSITIONS

[75] Inventor: John R. Wietfeldt, Cincinnati, Ohio

[73] Assignee: The Proctor & Gamble Company, Cincinnati, Ohio

[*] Notice: The portion of the term of this patent subsequent to Apr. 28, 2005 has been disclaimed.

[21] Appl. No.: 230,553

[22] Filed: Aug. 10, 1988

[51] Int. Cl.$^5$ .............................................. A61K 7/18
[52] U.S. Cl. ........................................................ 424/52
[58] Field of Search .......................................... 424/52

[56] References Cited

U.S. PATENT DOCUMENTS

| | | | |
|---|---|---|---|
| 2,956,480 | 5/1976 | Dichter et al. | 424/54 |
| 2,975,102 | 3/1961 | Matsumura et al. | 167/93 |
| 3,429,963 | 2/1969 | Shedlowky | 424/56 |
| 3,888,976 | 6/1975 | Milkvy et al. | 424/44 |
| 4,097,935 | 7/1978 | Jarcho | 3/1.9 |
| 4,146,606 | 3/1979 | Yamaga et al. | 424/52 |
| 4,183,914 | 1/1980 | Gaffar et al. | 424/48 |
| 4,217,342 | 8/1980 | Gaffar et al. | 424/48 |
| 4,217,343 | 8/1980 | Gaffar et al. | 424/48 |
| 4,235,633 | 11/1980 | Tomioka et al. | 106/35 |
| 4,254,101 | 3/1981 | Denny | 424/52 |
| 4,288,355 | 9/1981 | Anderson | 523/116 |
| 4,304,766 | 12/1981 | Chang | 424/52 |
| 4,358,559 | 11/1982 | Holcomb | 524/380 |
| 4,367,219 | 1/1983 | Schole | 424/52 |
| 4,407,984 | 10/1983 | Ratcliff et al. | 522/14 |
| 4,415,549 | 11/1983 | Shah et al. | 424/52 |
| 4,419,346 | 12/1983 | Stroz et al. | 424/151 |
| 4,430,324 | 2/1984 | Viccaro | 424/52 |
| 4,482,535 | 11/1984 | Sugar et al. | 424/49 |
| 4,591,384 | 5/1986 | Akaheng | 106/35 |
| 4,627,977 | 12/1986 | Gaffar et al. | 424/52 |
| 4,647,600 | 3/1987 | Kawahara | 106/35 |
| 4,661,341 | 4/1987 | Benedict et al. | 424/48 |
| 4,716,035 | 12/1987 | Sampathkumar | 424/52 |
| 4,806,340 | 2/1989 | Gaffar et al. | 424/52 |
| 4,806,342 | 2/1989 | Gaffar et al. | 424/52 |
| 4,808,400 | 2/1989 | Gaffar et al. | 424/52 |
| 4,808,401 | 2/1989 | Gaffar et al. | 424/52 |
| 4,826,675 | 5/1989 | Gaffar et al. | 424/52 |
| 4,871,531 | 10/1989 | Hartlaub et al. | 424/52 |

FOREIGN PATENT DOCUMENTS 0233059 8/1987 European Pat. Off. .
721898 9/1972 South Africa .

OTHER PUBLICATIONS

*Journal of Dental Research* (1982) 61 (3) 451–455.
*Journal of Dental Research* (1983) 62 (10) 1049–1053.
Featherstone, J. D. B., "Remineralization of Artificial Carious Lesions in vivo and in vitro", Proceedings of Workshop (1983), IRL Press Ltd.

*Primary Examiner*—Shep K. Rose
*Attorney, Agent, or Firm*—Douglas C. Mohl; Jack D. Shaeffer; Richard C. Witte

[57] ABSTRACT

Oral compositions containing a linear polymer polyelectrolyte, a soluble fluoride ion source and a strontium ion source are described herein.

7 Claims, No Drawings

ORAL COMPOSITIONS

TECHNICAL FIELD

The present invention relates to oral compositions which provide more efficient fluoride uptake by the enamel of human teeth.

BACKGROUND OF THE INVENTION

The role of fluoride in the remineralization of carious lesions is well known. The use of agents to enhance this benefit is also well known. One such agent is strontium.

While strontium's inclusion in oral compositions containing fluoride is desirable, the agents tend to form an insoluble precipitate unless separated before use or the strontium ions are complexed so as not to be available to form the precipitate. Strontium EDTA is such a complex.

The effect of strontium-EDTA complex in combination with sodium recinoleate and a fluoride source is found in the Journal of Dental Research (1982) 61 (3) 451–455. The combined effect of strontium and fluoride in reducing the acid solubility of enamel is also disclosed in the Journal of Dental Research (1983) 62 (10) 1049–1053. A further reference discussing the effect of strontium and fluoride is Featherstone, J. D. B., "Remineralization of Artificial Carious Lesions In-vivo and In-vitro", Proceedings of Workshop. (1983) IRL Press Ltd.

The use of strontium in combination with fluoride in oral compositions is also disclosed in a number of patent references. Included among these references are U.S. Pat. No. 3,888,976, June 10, 1975 to Mlkvys disclosing an effervescent mouthwash tablet containing strontium ions and possibly a fluoride ion source. U.S. Pat. No. 4,367,219, Jan. 4, 1983 to Schole discloses dentifrices containing a combination of strontium EDTA, a recinoleate salt and a fluoride ion source. U.S. Pat. No. 4,415,549, Nov. 15, 1983 to Shah et al. discloses toothpastes containing a glycyrrhizinate salt, strontium EDTA and a fluoride ion source. Finally European Patent Application No. 0,079,611, June 6, 1983, Shah, discloses oral compositions containing a strontium EDTA complex and a fluoride ion source.

The use of other materials in oral compositions to provide a variety of benefits in combination with soluble fluoride ion sources has also been disclosed in the patent literature.

Included are certain polymers and other agents. Specific agents disclosed are polyelectrolytes such as copolymers of maleic anhydride and ethylene disclosed in U.S. Pat. No. 3,429,963, Feb. 25, 1969 to Shedlovsky. Shedlovsky also discloses polyacrylic acid having an average molecular weight of 1500 and greater. Other references disclosing polyacrylic acids in oral compositions are South African Pat. No. 720898. Sept. 12, 1972 which discloses such acids having a molecular weight of from 1000 to 1,000,000; and U.S. Pat. No. 4,304,766, Dec. 8, 1971 to Chang discloses polyacrylic acid having a molecular weight in the range of 2,000 to 4,000,000 for use as a membrane to prevent the elution from teeth of previously applied agents. Finally, U.S. Pat. No. 3,956,480, to Gaffar, May 11, 1976 discloses complexes of anionic polymers (e.g., acrylic acid) and a cationic therapeutic agent (e.g., chlorhexidine) as anticalculus agents.

In spite of the many disclosures of strontium, fluoride ions and linear polymeric polyelectrolytes in the prior art, there is lacking a suggestion to combine these agents in a single oral composition. Strontium ions form a complex with the polycarboxylate or polysulfonate thereby not being able to form a precipitate with fluoride.

It is therefore an object of the present invention to provide oral compositions which combine a linear polymeric polyelectrolyte such as a polycarboxylate or polysulfonate or copolymers, strontium and fluoride.

It is a further object of the present invention to provide a more effective anti-caries composition.

It is still a further object of the present invention to provide a more effective method of applying fluoride to tooth enamel and dentin.

These and other objects will become more clear from the detailed description which follows.

All percentages and ratios used herein are by weight and all measurements are made at 25° C. unless otherwise specified.

SUMMARY OF THE INVENTION

The present invention embraces oral compositions comprising:
(a) a safe and effective amount of a linear polymeric polycarboxylate, polysulfonate, polysulfate or copolymers thereof;
(b) a safe and effective amount of a strontium ion source;
(c) a safe and effective amount of a fluoride ion source; and
(d) an orally acceptable carrier, wherein said composition is substantially free of linear, non-crosslinked polyacrylic acid polymers or copolymers.

The present invention also encompasses a method for retarding the development of dental caries.

DETAILED DESCRIPTION OF THE INVENTION

The compositions of the present invention comprise polycarboxylic acid and polysulfonic acid polymers or copolymers, a strontium ion source, a fluoride ion source and a pharmaceutically acceptable carrier.

By "oral compositions" as used herein means a product which in the ordinary course of usage is not intentionally swallowed for purposes of systemic administration of particular therapeutic agents, but is rather retained in the oral cavity for a time sufficient to contact substantially all of the dental surfaces and/or oral tissues for purposes of oral activity.

By "safe and effective amount" as used herein means sufficient amount of material to provide the desired benefit while being safe to the hard and soft tissues of the oral cavity.

By the term "comprising", as used herein, is meant that various additional components can be conjointly employed in the compositions of this invention as long as the listed materials perform their intended functions.

By the term "carrier", as used herein, is meant a suitable vehicle which can be used to apply the present compositions in the oral cavity.

Linear Polymeric Polycarboxylate, Polysulfonate, Polysulfate or Copolymers

The linear polymeric polycarboxylates, polysulfonate, polysulfate, or polymers are staple items of commerce. Generally suitable are polymerized olefinically or ethylenically unsaturated carboxylic, sulfonic, or sulfuric acids containing an activated carbon-to-carbon olefinic double bond and at least one carboxyl, sulfonic or sulfuric group, that is, an acid containing an olefinic double bond which readily functions in polymerization because of its presence in the monomer molecular either in the alpha-beta position with respect to the acidic group or as part of a terminal methylene grouping. Illustrative of such acids are crotonic, sorbic, alpha-chlorsorbic, cinnamic, muconic, itaconic, citraconic, mesaconic, glutaconic, aconitic, angelic, umbellic, fumaric, maleic acids and anhydrides. Other different olefinic monomers copolymerizable with such carboxylic monomers include vinylacetate, vinyl chloride, dimethyl maleate and the like. Copolymers contain sufficient carboxylic salt groups for water-solubility.

Included in such polymers are copolymers of malic acid or anyhydride with another monomer such as methyl vinyl ether. The monomer ratio can be in the range of 1:4 to 4:1 and the molecular weight in the range of 30,000 to about 1,000,000.

Additional operative polymeric polycarboxylates disclosed in above referred to U.S. Pat. Nos. 4,138,477 and 4,183,914, include copolymers of maleic anhydride with styrene, isobutylene or ethyl vinyl ether, polyacrylic polyitaconic and polymaleic acids, and sulfoacrylic oligomers of molecular weight as low as 1,000, available as Uniroyal ND-2.

Illustrative of acids capable of polymerizing to form polysulfonates are styrene sulfonic acid, or its sodium or potassium salts, and ethylene sulfonic acid or its sodium salt.

The molecular weight of the polymer may be in the range of about 1000 to about 1,200,000 (mass average), preferably the molecular weight is from about 4000 to about 10,000, most preferably from about 4300 to about 5200.

The amount of the polymer used in the present compositions is generally from about 0.0003% to about 13%, preferably from about 0.03% to about 5.0%, most preferably from about 0.03% to about 4%. For a dentifrice composition containing about 220 ppm $Sr^{++}$ the preferred level of polymer is from about 0.3% to about 0.5%. For a mouthwash composition containing about 225 ppm $Sr^{++}$ the preferred polymer level is from about 0.03% to about 0.10%. Mixtures of the polymers or copolymers are also useful in the present invention.

Strontium Ion Source

The strontium ions of the present compositions can be provided by any of a wide variety of strontium salts or complexes. Included are strontium chloride, strontium acetate, strontium bromide, strontium glyconate, strontium lactate, strontium hydroxide and strontium salicylate. In another execution strontium can be provided to the present compositions as a complex with the polyelectrolyte. The strontium ion source is soluble enough in the composition at 25° C. or when used to provide from about 150 to about 10,000, preferably from about 500 to about 4400 ppm $Sr^{++}$.

Fluoride Ion Source

The water-soluble fluoride compound is present in the compositions of this invention in an amount sufficient to give a fluoride concentration of from about 0.0025% to about 5.0% by weight, preferably from about 0.005% to about 2.0% by weight at 25° C., in the composition or when used to provide anticaries effectiveness. Preferred fluorides are sodium fluoride, stannous fluoride, indium fluoride, acidulated phosphate fluoride and sodium monofluorophosphate. U.S. Pat. No. 2,946,735, July 26, 1960 to Norris et al. and U.S. Pat. No. 3,678,154, July 18, 1972 to Widder et al. disclose such salts as well as others. These references are incorporated herein by reference.

Orally Acceptable Carrier

The carrier for the components of the present invention can be any vehicle suitable for use in the oral cavity. Such carriers include the usual components of mouthwashes, toothpastes, topical dental gels, toothpowders, prophylaxis pastes, lozenges, gums and the like and are more fully described hereinafter. Dentifrices and mouthwashes are the preferred systems with toothpastes being the more preferred.

Toothpastes contain as a major component an abrasive. The abrasive polishing material contemplated for use in the present invention can be any material which does not excessively abrade dentin. These include, for example, silicas including gels and precipitates, calcium carbonate, dicalcium orthophosphate dihydrate, calcium pyrophosphate, tricalcium phosphate, calcium polymetaphosphate, insoluble sodium polymetaphosphate, hydrated alumina, and resinous abrasive materials such as particulate condensation products of urea and formaldehyde, and others such as disclosed by Cooley et al. in U.S. Pat. No. 3,070,510, Dec. 25, 1962, incorporated herein by reference. Mixtures of abrasives may also be used.

Silica dental abrasives, of various types, can provide the unique benefits of exceptional dental cleaning and polishing performance without unduly abrading tooth enamel or dentin. Silica abrasive materials are also exceptionally compatible with sources of soluble fluoride. For these reasons they are preferred for use herein. Of course the abrasive selected should also exhibit excellent compatibility with soluble strontium ion sources.

The silica abrasive polishing materials useful herein, as well as the other abrasives, generally have an average particle size ranging between about 0.1 and 30 microns, preferably 5 and 15 microns. The silica abrasive can be precipitated silica or silica gels such as the silica xerogels described in Pader et al., U.S. Pat. No. 3,538,230, issued March 2, 1970 and DiGiulio, U.S. Pat. No. 3,862,307, June 21, 1975, both incorporated herein by reference. Preferred are the silica xerogels marketed under the tradename "Syloid" by the W. R. Grace & Company, Davison Chemical Division. Preferred precipitated silica materials include those marketed by the J. M. Huber Corporation under the tradename, "Zeodent", particularly the silica carrying the designation "Zeodent 119". These silica abrasive are described in U.S. Pat. No. 4,340,583, July 29, 1982, incorporated herein by reference.

The abrasive in the dentifrice compositions described herein is present at a level of from about 6% to about 70%, preferably from about 15% to about 25% when the dentifrice is a toothpaste. higher levels, as high as 90%, may be used if the composition is a toothpowder.

Flavoring agents can also be added to the dentifrice and other compositions of the present invention. Suitable flavoring gents include oil of wintergreen, oil of peppermint, oil of spearmint, oil of sassafras, and oil of clove. Sweetening agents are also useful and include aspartame, acesulfame, saccharin, dextrose, levulose and sodium cyclamate. Flavoring and sweetening agents are generally used in the compositions herein at levels of from about 0.005% to about 2% by weight.

The compositions of this invention also contain emulsifying agents. Suitable emulsifying agents are those which are reasonably stable and foam throughout a wide pH range, including non-soap anionic, nonionic, cationic, zwitterionic and amphoteric organic synthetic detergents. Many of these suitable surfactants are disclosed by Gieske et al. in U.S. Pat. No. 4,051,234, Sept. 27, 1977 incorporated herein by reference.

Water is also present in the compositions of this invention. Water employed in the preparation of commercially suitable compositions should preferably be deionized and free of organic impurities. Water generally comprises from about 10% to 50%, preferably from about 20% to 40%, by weight of the toothpaste compositions herein. These amounts of water include the free water which is added plus that which is introduced with other materials such as with sorbitol.

In preparing toothpastes, it is necessary to add some thickening material to provide a desirable consistency. Preferred thickening agents are carboxyvinyl polymers, carrageenan, hydroxyethyl cellulose and water soluble salts of cellulose ethers such as sodium carboxymethyl cellulose and sodium carboxymethyl hydroxyethyl cellulose. Natural gums such as gum karaya, gum arabic, and gum tragacanth and polysaccharide gums such as xanthan gum can also be used. Colloidal magnesium aluminum silicate or finely divided silica can be used as part of the thickening agent to further improve texture. Thickening agents in an amount from 0.5% to 5.0% by weight of the total composition may be used.

It is also desirable to include a humectant in a toothpaste to keep it from hardening. Suitable humectants include glycerin, sorbitol, and other edible polyhydric alcohols at a level of from about 10% to about 70%.

Another preferred embodiment of the present invention is a mouthwash composition. Conventional mouthwash composition components can comprise the carrier for the actives of the present invention. Mouthwashes generally comprise from about 20:1 to about 2:1 of a water/ethyl alcohol solution and preferably other ingredients such as flavor, sweeteners, humectants and sudsing agents such as those described above. The humectants, such as glycerin and sorbitol give a moist feel to the mouth. Generally, on a weight basis the mouthwashes of the invention comprise 5% to 60% (preferably 10% to 25%) ethyl alcohol, 0% to 20% (preferably 5% to 20%) of a humectant, 0% to 2% (preferably 0.01% to 0.15%) emulsifying agent, 0% to 0.5% (preferably 0.005% to 0.06%) sweetening agent such as saccharin, 0% to 0.3% (preferably from 0.03% to 0.3%) flavoring agent, and the balance water.

Suitable lozenge and chewing gum components are disclosed in U.S. Pat. No. 4,083,955, April 11, 1978 to Grabenstetter et al., incorporated herein by reference.

Suitable topical dental gels generally comprise a base of a humectant such as glycerine thickened with a suitable agent. Such gels generally do not contain an abrasive.

The pH of the present compositions and/or its pH in the mouth can be any pH which is safe for the mouth's hard and soft tissues. Such pH's are generally from about 3 to about 10, preferably from about 4 to about 8. The present compositions, since they are designed to deliver fluoride to tooth enamel, should not contain materials which would cause significant loss of strontium and/or fluoride ions.

By "substantially free of linear, non-crosslinked acrylic acid polymers or copolymers" is meant less than about 2.5%.

METHOD OF MANUFACTURE

The carrier compositions of the present invention can be made using methods which are common in the oral products area. However the strontium ion source and the linear polymeric polycarboxylate, polysulfonate, or polysulfate should be added prior to the addition of the fluoride ion source. This is to ensure that strontium and fluoride do not form an insoluble precipitate. A specific method of manufacture is set forth in the Examples.

COMPOSITION USE

The present invention in its method aspect involves applying to the oral cavity safe and effective amounts of the compositions described herein. These amounts (e.g. from about 0.3 to about 15 g), if it is a toothpaste or mouthwash, are kept in the mouth for from about 15 to about 60 seconds.

The following examples further describe and demonstrate preferred embodiments within the scope of the present invention. The examples are given solely for illustration and are not to be construed as limitations of this invention as many variations thereof are possible without departing from the spirit and scope thereof.

EXAMPLE I

The composition given below is exemplary of the present invention.

| Component | Weight % |
| --- | --- |
| Sodium Fluoride | 0.243 |
| Strontium Chloride 6H$_2$O | 0.667 |
| Silica Dental Abrasive[1] | 20.000 |
| Methylvinylether/Maleic Acid Copolymer[2] | 2.200 |
| Sodium Saccharin | 0.130 |
| Titanium Dioxide | 0.700 |
| Flavor | 0.600 |
| Carboxymethylcellulose | 0.600 |
| Surfactant-Tween 80[3] | 0.900 |
| Polyethyleneglycol MW 600 | 5.000 |
| Triethanolamine | 1.000 |
| Dye | 0.050 |
| Water | 19.000 |
| Sorbitol (70% Aqueous Solution) | q.s. 100% |

[1]Precipitated silica abrasive offered by J. M. Huber Company as Zeodent-119
[2]Polymer having mass average molecular weight of about 50,000
[3]POE (20) sorbitan monooleate offered by ICI Americas Inc.

The above composition is prepared by putting 50% of the sorbitol into a main mix tank, adding all of the polymeric polycarboxylate and 50% of the water and mixing for a few minutes. Strontium chloride is then dissolved in 10% of the water and added to the main mix tank with the desired pH being obtained by immediately adding HCl or NaOH. Next sodium fluoride is dissolved in the remaining water and added to the main mix tank, followed by the silica abrasive, sodium saccharin, titanium dioxide and flavor. In a separate tank, the binder is mixed with the remaining sorbitol and added to the main mix tank followed by the surfactant and the dye. The final mixture is heated to 70° C., processed through a mill and deaerated if necessary.

EXAMPLE II

Given below is another example of the present invention.

| Component | Weight % |
| --- | --- |
| Sodium Fluoride | 0.111 |
| Strontium Chloride 6H$_2$O | 0.333 |
| Silica Dental Abrasive[1] | 20.000 |
| Gantrez (S-97)[2] | 0.200 |
| Sodium Saccharin | 0.130 |
| Titanium Dioxide | 0.100 |
| Flavor | 0.600 |
| Carboxymethylcellulose | 0.600 |
| Sodium Alkyl Sulfate | 2.500 |
| Dye | 0.050 |
| Water | 19.000 |
| Sorbitol (70% Aqueous Solution) | q.s. 100% |

[1]Precipitated silica abrasive offered by J. M. Huber Company as Zeodent-119
[2]A copolymer of methylvinylether and maleic anhydride having a molecular weight of about 1,000,000

EXAMPLE III

Given below is yet another example of the present invention.

| Component | Weight % |
| --- | --- |
| Sodium Fluoride | 0.243 |
| Strontium Chloride 6H$_2$O | 0.166 |
| Silica Dental Abrasive[1] | 20.000 |
| Polystyrene Sulfonate[2] | 2.600 |
| Sodium Saccharin | 0.130 |
| Titanium Dioxide | 0.700 |
| Flavor | 0.600 |
| Carboxymethylcellulose | 0.600 |
| Sodium Lauroyl Sarcosinate | 1.500 |
| Dye | 0.050 |
| Water | 19.000 |
| Sorbitol (70% Aqueous Solution) | q.s. 100% |

[1]Precipitated silica abrasive offered by J. M. Huber Company as Zeodent-119
[2]Polymer having an average molecular weight of about 70,000

EXAMPLE IV

Given below is another composition representative of the present invention.

| Component | Weight % |
| --- | --- |
| Sodium Fluoride | 0.443 |
| Strontium Chloride 6H$_2$O | 1.200 |
| Silica Dental Abrasive[1] | 20.000 |
| Gantrez (S-97)[2] | 7.200 |
| Sodium Saccharin | 0.130 |
| Titanium Dioxide | 0.100 |
| Flavor | 0.600 |
| Carboxymethylcellulose | 0.600 |
| Cocoyl Isethionate | 2.000 |
| Dye | 0.050 |
| Water | 19.000 |
| Sorbitol (70% Aqueous Solution) | q.s. 100% |

[1]Precipitated silica abrasive offered by J. M. Huber Company as Zeodent-119
[2]A copolymer of methylvinylether and maleic anhydride having a molecular weight of 1,000,000

All of the above compositions provide improved fluoride uptake by dental enamel. Similar performance is obtained if the polyelectrolyte is replaced by another linear polymeric polycarboxylate, polysulfonate or copolymer having a molecular weight of from about 1000 to about 1,200,000. Similarly strontium chloride may be replaced with another strontium salt such as strontium acetate, strontium lactate, strontium salicylate, strontium hydroxide or strontium glyconate.

Fluoride Uptake Analysis

The ability of compositions of the present invention to deliver enhanced fluoride to dental enamel was measured using an in-vitro enamel disc method.

Enamel discs (4 mm diameter) were mounted in lucite rods, then ground and polished—removing at least 40 um of the enamel surface. Discs were decalcified for 46 hours at 37° C. in 8 ml of 0.1 M lactic acid plus $1.0 \times 10^{-4}$ M disodium-methanehydroxydiphosphonate (MHDP) adjusted to pH 4.5. The depth of demineralization was approximately 100 um. The discs were placed in groups of four (4) per treatment group.

At the beginning of the study, each treatment group was suspended for one (1) hour in 15 grams of fresh, paraffin stimulated, pooled human saliva under constant agitation. The treatment groups were then exposed to 20 ml of an appropriate test solution for one (1) minute, followed by a thorough rinsing in deionized water. The one minute treatment was followed by one (1) hour soaking in the saliva baths. This cyclic pattern (one minute treatment/thorough rinse/one hour saliva soak) was repeated seven (7) times a day for four (4) days for a total of twenty-eight (28) treatments. Saliva baths were changed twice daily to maintain their freshness. At the end of each day, the discs were thoroughly rinsed with deionized water and placed upright in a moist atmosphere under refrigeration in order to minimize any microbial growth.

Following the 28th treatment, specimens were thoroughly rinsed with dionized water and analyzed for fluoride content using a microdrill biopsy technique. In this technique, a carbide dental bar (diameter approximately 0.45 mm) penetrates the surface of the discs and travels to the base of the demineralized are, in this case 100 um. The displaced enamel powder is recovered into a small polyethylene vial, where it is dissolved with 20 ul of 0.5 M HClO$_4$. To this is added 40 ul of deionized water, then 40 ul of a Citrate-EDTA buffer resulting in a total volume of 100 ul for analysis. Fluoride analysis of this solution is done using an Orion Fluoride Ion-specific electrode (Model 96-09-00) that has been appropriately calibrated for the range of these analytical samples.

Statistical analyses were done using a standard t- test for significance.

Using the above described procedure, various strontium ion concentrations and polyelectrolyte polymer levels were used with 1100 ppm F$^-$ to determine the amount of F[31] taken up by the enamel.

| | Treatment Solutions* | | |
| --- | --- | --- | --- |
| Sr$^{++}$ (PPM) | F$^-$ (PPM) | Gantrez (Wt. %) | F$^-$ Uptake ng/cm$^2$)** |
| 0 | 1100 | 0 | 21.66 ± 1.03 |
| 0 | 1100 | 0.24 | 22.31 ± 0.73 |
| 0 | 1100 | 0.80 | 23.71 ± 1.78 |
| 300 | 1100 | 0.24 | 26.01 ± 1.90 |
| 1000 | 1100 | 0.80 | 26.18 ± 2.05 |
| 0 | 2800 | 0 | 35.29 ± 1.02 |
| 2000 | 1100 | 0.80 | 36.63 ± 3.57 |

*These numbers represent the equivalents in whole dentifrice before dilution. Actual levels in test solutions were at ¼ these levels.
**Means outside brackets are significantly different at α = 0.05.

What is claimed is:

1. An oral composition in the form of a toothpaste comprising:
   (a) a safe and effective amount of a copolymer of vinyl methyl ether and maleic anhydride;
   (b) a safe and effective amount of a soluble strontium ion source; and
   (c) a safe and effective amount of a soluble fluoride ion source;
   wherein said composition is substantially free of linear, noncrosslinked acrylic acid polymers or copolymers.

2. An oral composition according to claim 1 wherein the polymer is present at a level of from about 0.0003% to about 13%.

3. An oral composition according to claim 2 wherein the soluble strontium ion source is present at a level of from about 2 to about 10,000 ppm $Sr^{++}$ in the composition and/or when it is used.

4. An oral composition according to claim 3 which also contains a silica dental abrasive.

5. An oral composition according to claim 4 wherein the soluble fluoride ion source is sodium fluoride present at a level sufficient to give from about 25 to about 5000 ppm $F^-$ in the composition and/or when it is used.

6. A method of applying fluoride to tooth enamel/dentin comprising applying a safe and effective amount of the composition according to claim 1 to the enamel/dentin.

7. A method according to claim 6 wherein the composition is according to claim 5.

* * * * *